US011253370B2

(12) United States Patent
Scott-Young

(10) Patent No.: US 11,253,370 B2
(45) Date of Patent: Feb. 22, 2022

(54) VERTEBRAL COLUMN IMPLANT

(71) Applicant: Prism Surgical Designs Pty Ltd., Red Hill (AU)

(72) Inventor: Matthew Norman Scott-Young, Red Hill (AU)

(73) Assignee: PRISM SURGICAL DESIGNS PTY LTD., Red Hill (AU)

( * ) Notice: Subject to any disclaimer, the term of this patent is extended or adjusted under 35 U.S.C. 154(b) by 105 days.

(21) Appl. No.: 16/198,207

(22) Filed: Nov. 21, 2018

(65) Prior Publication Data

US 2019/0159909 A1 May 30, 2019

(30) Foreign Application Priority Data

Nov. 24, 2017 (AU) ................. 2017904750
Aug. 2, 2018 (AU) ................. 2018902812

(51) Int. Cl.
*A61F 2/44* (2006.01)
*A61F 2/30* (2006.01)

(52) U.S. Cl.
CPC .......... *A61F 2/442* (2013.01); *A61F 2/30771* (2013.01); *A61F 2/4455* (2013.01); *A61F 2/4465* (2013.01); *A61F 2002/30331* (2013.01); *A61F 2002/30599* (2013.01); *A61F 2002/30785* (2013.01); *A61F 2002/30932* (2013.01)

(58) Field of Classification Search
CPC ...................................... A61F 2/442
See application file for complete search history.

(56) References Cited

U.S. PATENT DOCUMENTS

| 5,192,327 | A | 3/1993 | Brantigan | |
|---|---|---|---|---|
| 2004/0122518 | A1* | 6/2004 | Rhoda | A61F 2/4611 623/17.11 |
| 2010/0125334 | A1* | 5/2010 | Krueger | A61F 2/447 623/17.16 |
| 2012/0265303 | A1* | 10/2012 | Refai | A61F 2/4465 623/17.11 |

(Continued)

*Primary Examiner* — Tessa M Matthews
(74) *Attorney, Agent, or Firm* — Knobbe, Martens, Olson & Bear, LLP

(57) ABSTRACT

A vertebral column implant assembly for insertion between two vertebrae, the assembly comprising: a superior implant body for engagement with a superior vertebra; an inferior implant body for engagement with an inferior vertebra; a central implant body adapted to be positioned in between the superior implant body and the inferior implant body, the central implant body further comprising: a first fastening arrangement positioned on an upper face of the central implant body to engage and fasten the superior implant body; and a second fastening arrangement positioned on a lower face of the central implant body to engage and fasten the inferior implant body; wherein each of the central implant body, the superior implant body and the inferior implant body comprises internal walls defining respective passages, such that the first and second fastening arrangements are positioned along inner marginal portions of the superior and inferior implant bodies respectively and structured to engage the central body with the superior and inferior implant bodies respectively to interconnect each of the respective passages to form a continuous passage to allow graft material to be positioned therein.

16 Claims, 6 Drawing Sheets

(56) References Cited

U.S. PATENT DOCUMENTS

| | | | |
|---|---|---|---|
| 2012/0316651 A1* | 12/2012 | Ullrich, Jr. | A61F 2/4455 |
| | | | 623/17.16 |
| 2014/0094919 A1 | 4/2014 | Mantri | |
| 2015/0320568 A1* | 11/2015 | Ameil | A61F 2/4611 |
| | | | 623/17.13 |
| 2016/0158023 A1* | 6/2016 | Klimek | A61F 2/442 |
| | | | 623/17.16 |
| 2016/0374829 A1 | 12/2016 | Vogt et al. | |
| 2018/0098861 A1 | 4/2018 | Howard et al. | |
| 2019/0201208 A1* | 7/2019 | Yu | A61F 2/442 |
| 2019/0328539 A1* | 10/2019 | Suh | A61F 2/447 |

* cited by examiner

VERTEBRAL COLUMN IMPLANT

TECHNICAL FIELD

The present invention relates to orthopaedic implants and particularly to a vertebral column implant for surgeries such as corpectomy surgery.

BACKGROUND

Any references to methods, apparatus or documents of the prior art are not to be taken as constituting any evidence or admission that they formed, or form part of the common general knowledge.

Spinal Column Tumour/Trauma/Degeneration plus/minus impingement of the spinal cord and nerve roots, respectively, are conditions that may typically warrant corpectomy spinal surgery. In severe cases of multilevel deformity or degeneration, corpectomies are often performed.

Current systems on the market involve an expandable or many smaller pieces that are 'joined and built' together to reconstruct and fill the measured anterior spinal deficit that exists from the surgical vertebral body excision.

Most modern vertebral column implant systems are expandable or stackable in nature. Expandable style devices are commonly surgically expanded insitu. These systems often lack adequately packed and compressed bone graft material necessary for effective spinal fusion. Another common vertebral column replacement system comprises small, individual components stacked together. The central graft space or window for graft material placement is often compromised due to the housing assembly such as a 'bolt and nut' or similar central connection assembly housed within the implant material. A central grafting space is commonly present to pack grafting material or similar. If the said graft space is limited in volume it may inhibit a successful spinal fusion and thereby contribute to device subsidence. The prevention of subsidence and promotion of a successful fusion mass can assist in the prevention of revision surgeries and/or post-operative complications.

SUMMARY OF INVENTION

In an aspect, the invention provides a vertebral column implant assembly for insertion between two vertebrae, the assembly comprising:
a superior implant body for engagement with a superior vertebra;
an inferior implant body for engagement with an inferior vertebra;
a central implant body adapted to be positioned in between the superior implant body and the inferior implant body, the central implant body further comprising:
a first fastening arrangement positioned on an upper face of the central implant body to engage and fasten the superior implant body; and
a second fastening arrangement positioned on a lower face of the central implant body to engage and fasten the inferior implant body;
wherein each of the central implant body, the superior implant body and the inferior implant body comprises internal walls defining respective passages, such that the first and second fastening arrangements are positioned along inner marginal portions of the superior and inferior implant bodies respectively and structured to engage the central body with the superior and inferior implant bodies respectively to interconnect each of the respective passages to form a continuous passage to allow graft material to be positioned therein.

In an embodiment, the first arrangement of the central implant body further comprises: a first plurality of projection formations adapted to be inserted into projection receiving portions positioned along an in-use lower portion of the superior implant body; and wherein the second fastening arrangement comprises a second plurality of projection formations adapted to be inserted into projection receiving portions positioned along an in-use upper portion of the inferior implant body.

In an embodiment, the first arrangement of the central implant body further comprises: a first plurality of receiving portions adapted to receive projection formations positioned along an in-use lower portion of the superior implant body; and wherein the second fastening arrangement comprises a second plurality of receiving portions adapted to receive projection formations positioned along an in-use upper portion of the inferior implant body.

In an embodiment, each of said first and second fastening arrangements is adapted for securing the central implant body to said superior and inferior implant bodies respectively to prevent relative movement between the central implant body and said superior and inferior implant bodies.

In an embodiment, each of said central implant body and said superior and inferior implant bodies comprises respective outer walls such that upon fastening the central implant body to the superior and inferior implant bodies, the respective outer walls become inter-connected to provide a continuous outer surface.

In an embodiment, the first fastening arrangement allows the superior implant body to be fastened to the central implant body in no more than one fastened orientation.

In an embodiment, the second fastening arrangement allows the inferior implant body to be fastened to the central implant body in no more than one fastened orientation.

In an embodiment, the superior and inferior implant bodies are interchangeable such that the first fastening arrangement is adapted to engage the inferior implant body; and wherein the second fastening arrangement is adapted to engage the superior implant body.

In an embodiment, each of said central implant body and the superior and inferior implant bodies comprises: a respective anterior portion having an anterior wall: a respective posterior portion having a posterior wall with opposed intermediation portions extending between said anterior and posterior portions.

In an embodiment, length for each of the anterior walls is greater than length for the posterior walls. In alternative embodiments, length for each of the anterior walls may be equal to length for the posterior walls.

In an embodiment, height for the anterior portion for the superior implant body is greater than height for posterior portion of the superior implant body. In alternative embodiments, height for the anterior portion for the superior implant body may be equal to height for posterior portion of the superior implant body.

In an embodiment, height for the anterior portion for the inferior implant body is greater than height for posterior portion of the inferior implant body. In an alternative embodiment, height for the anterior portion for the inferior implant body may be equal to height for posterior portion of the inferior implant body.

In an embodiment, each of the respective posterior portions of the said central implant body and the superior and inferior implant bodies comprises a posterior wall having a thickness t1 and wherein each of the respective anterior portions of the said central implant body and the superior and inferior implant bodies comprises an anterior wall having a thickness t1 is greater than t2.

In an embodiment, the vertebral column implant further comprises:

a first locking arrangement for locking the superior implant body to the central implant body and prevent relative movement therebetween; and a second locking arrangement for locking the inferior implant body to the central implant body and prevent relative movement therebetween.

In an embodiment, one or both of said locking arrangements comprises one or more projecting locking members adapted to be received into a corresponding locking recess defined by one or more recess walls.

In an embodiment, the locking member comprises a profiled locking portion adapted to be received and retained in a locking aperture located in one of said recess walls defining the locking recess such that the locking member can be press fitted into the locking recess thereby inter-locking the central implant body with the superior implant body and/or the inferior implant body.

In an embodiment, each of locking recesses are positioned in an in-use lower portion of the superior implant body and/or an in-use upper portion of the inferior implant body.

In an embodiment, each of said locking members is located in between said anterior and posterior portions of the central implant body and wherein the locking recesses are located in between the anterior and posterior portions of the superior implant body or the inferior implant body.

In an embodiment, the vertebral column implant comprises:

a first pair of spaced apart locking members located along an inner margin portion of the upper face of the central implant body; and a second pair of spaced apart locking members located along an inner margin portion of the lower face of the central implant body.

In an embodiment, each of said first and second pair of locking members are located in said intermediate portion of the central implant body.

In another embodiment, the vertebral column implant comprises:

a first pair of spaced apart locking members located along an inner margin portion of the lower portion of the superior implant body; and a second pair of spaced apart locking members located along an inner margin portion of the upper portion of the inferior implant body.

In an embodiment, each of said first and second pair of locking members are located in said intermediate portion of the superior implant body or the inferior implant body.

BRIEF DESCRIPTION OF THE DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to a number of drawings as follows.

DETAILED DESCRIPTION OF PREFERRED EMBODIMENTS

Figure 1:
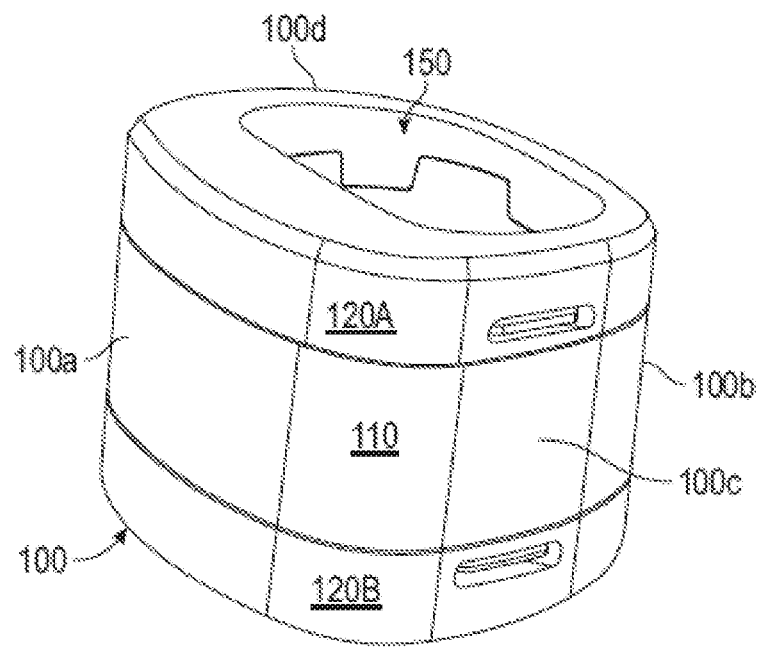
FIG. 1 is a first perspective view of a vertebral column implant assembly 100.

Referring to FIGS. 1 to 7, a vertebral column implant assembly 100 is illustrated. The implant assembly 100 is particularly well suited for insertion between two adjacent vertebrae (not shown) and comprises a stackable configuration. The implant assembly 100 comprises a central implant body 110 with an upper face 1101 (See FIG. 6B) that can be readily fastened to a superior implant body 120A by a first fastening arrangement. Similarly, the central implant body 110 also comprises a lower face 1102 (See FIG. 6B) that can readily fastened to an inferior implant body 120B by a second fastening arrangement. In the presently described embodiment, the overall configuration of each of the superior and inferior implant bodies 120A and 120B is identical. As a result, throughout the specification, reference numeral 120 generally refers to either the superior implant body 120A or the inferior implant body 120B.

Figure 5:
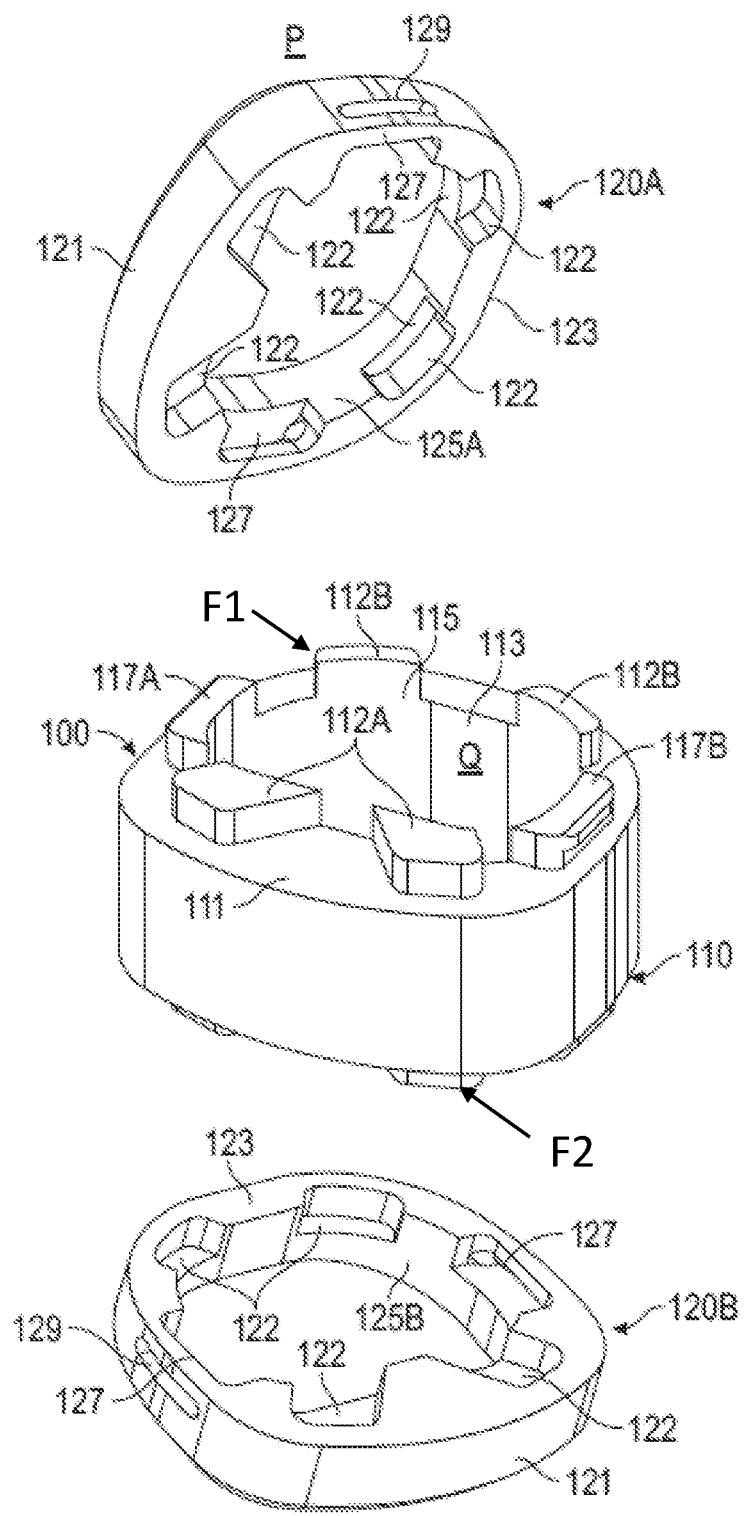
FIG. 5 is an exploded view of the vertical column implant assembly 100.
Figure 6A:
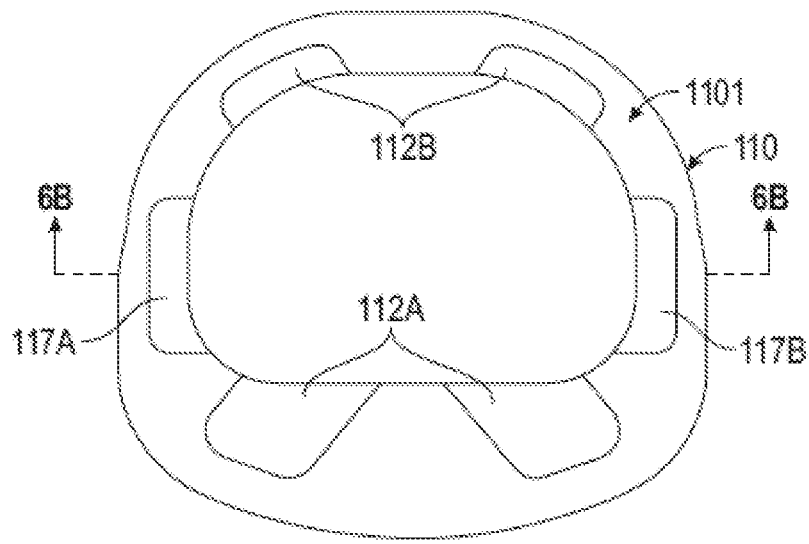
FIG. 6A is a top view of the central implant body 110.
Figure 6B:
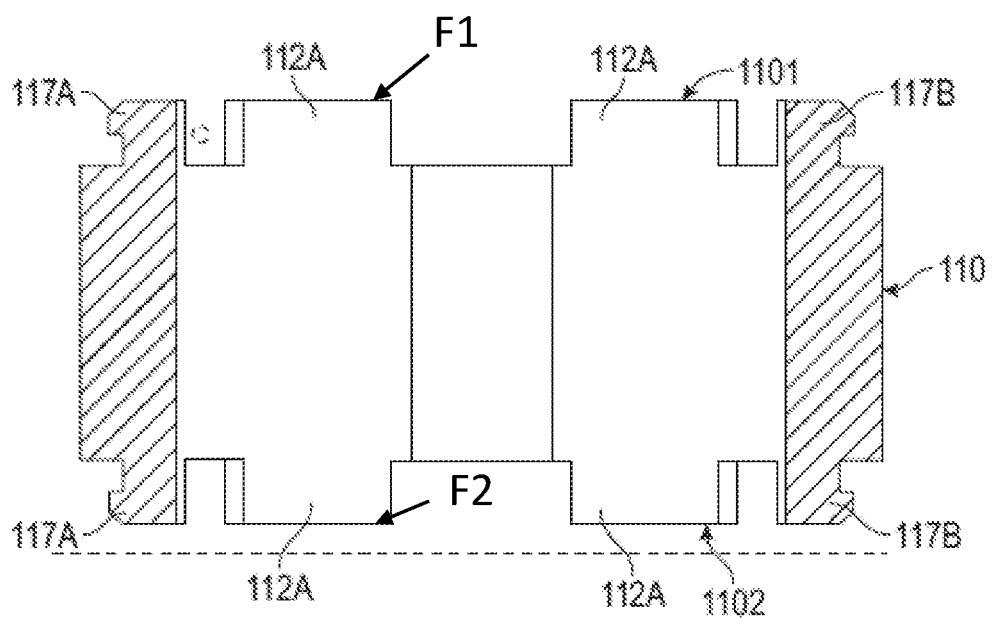
FIG. 6B is a sectional view of the central implant body 110 along section A-A (shown in FIG. 6A).

Referring to FIGS. 5, 6A and 6B, each of the central implant body 110 and the superior and inferior implant bodies 120A and 120B comprises respective internal passages 115 and 125A and 125B. The first and second fastening arrangements F1 and F2 on the upper and lower faces 1101 and 1102 are located circumferentially along an inner margin portion of the upper and lower faces 1101 and 1102. As a result, when the central implant body 110 is interlocked into engagement with the superior and inferior implant bodies 120A and 120B, the respective internal passages 115 and 125A and 125B respectively become interconnected to form a continuous passage 150. The inventors believe that the provision of the first and second fastening arrangements along an inner margin region of the upper and lower faces 1101 and 1102 of the central implant body 110 increases internal volume of the passage 150. As a result, during use, the passage 150 in the vertical column implant assembly 100 allows a greater quantity or volume of graft material to be positioned into the passage 150 thereby improving outcomes during procedures such as spinal fusion and contribute towards decreasing device subsidence.

Figure 2:
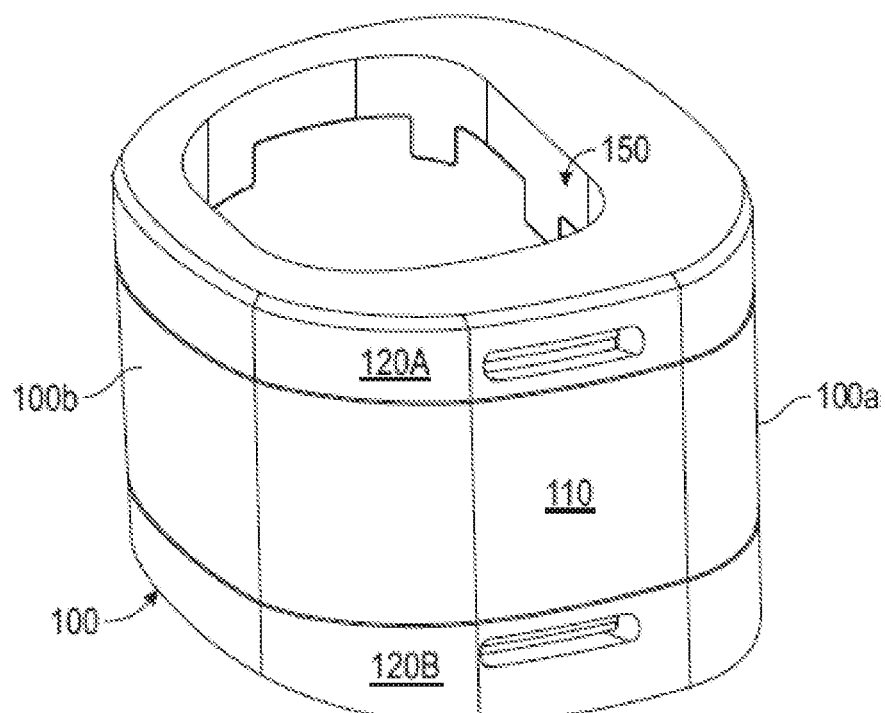
FIG. 2 is a second perspective view of the vertical column implant assembly 100.
Figure 3:
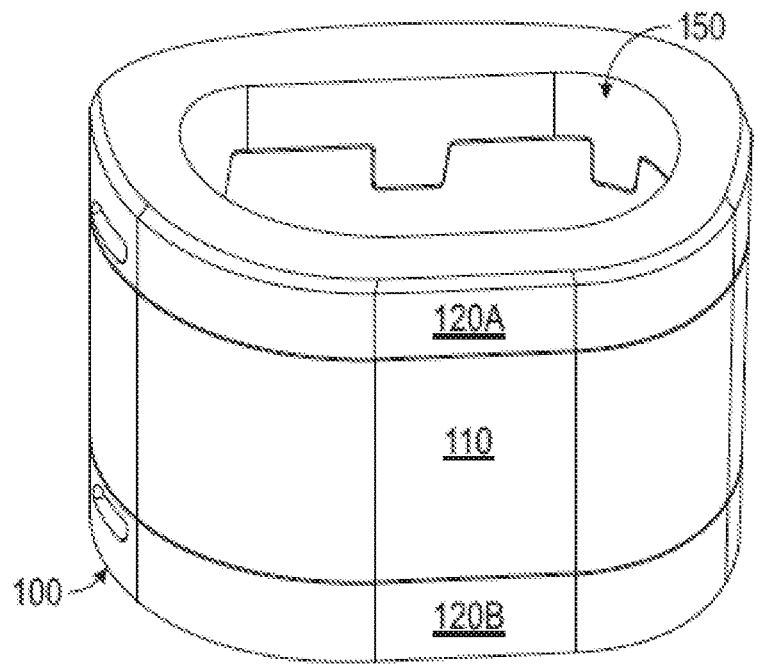
FIG. 3 is a posterior perspective view of the vertical column implant assembly 100.
Figure 4:
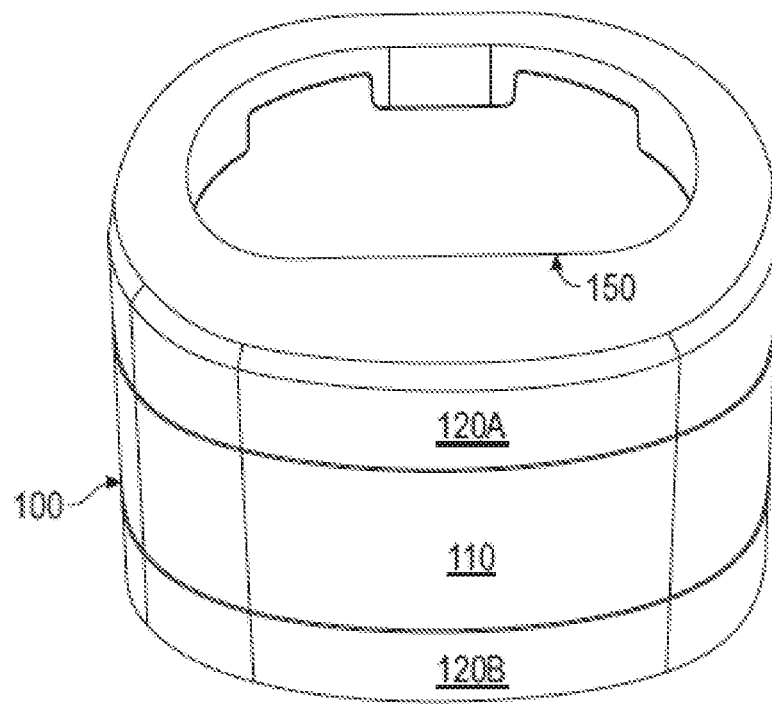
FIG. 4 is an anterior perspective view of the vertical column implant assembly 100.

Referring to FIGS. 1 and 2, in particular, the implant assembly 100 comprises an anterior portion or trailing edge 100a which is relatively thicker and greater in height in comparison with an opposing posterior portion 100b. Opposed intermediate portions 100c and 100d extend in between the opposed anterior and posterior portions 100a and 100b. The outer walls of the implant assembly 100, including each of the central implant body 110 and the superior and inferior implant bodies 120A and 120B, may have a lordotic angle to facilitate sagittal alignment. The implant assembly 100 has been structurally adapted to be positioned on the outer and posterior cortical rims of the vertebral endplate. The posterior portion 100b of the implant assembly 100, preferably including the posterior-lateral corners, may also be highly radiused or filleted, thus allowing for ease of implantation into the disc space. As a result, the posterior portion 100b may be provided with curved edges.

Figure 7A:
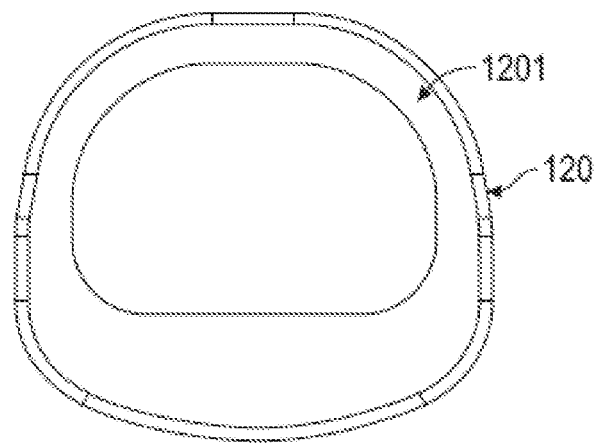
FIG. 7A is a view of the vertebra engaging face of the superior or inferior implant body 120.
Figure 7B:
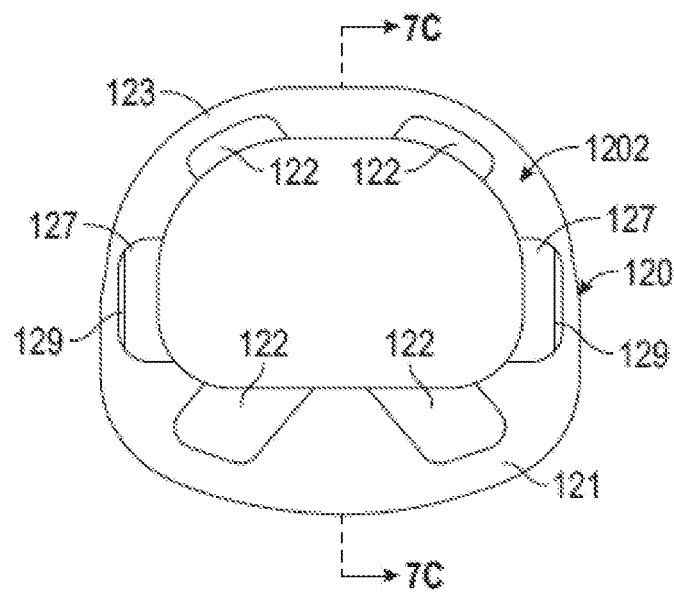
FIG. 7B is a second view of the implant engaging face of the superior or inferior implant body 120.
Figure 7C:
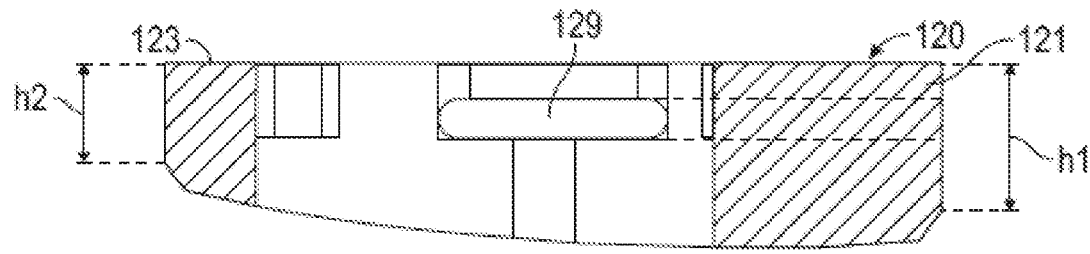
FIG. 7C is a sectional view along line B-B (shown in FIG. 7B).

Referring to FIGS. 7A to 7C, the overall height (h1) for the anterior portion 121 for the superior or inferior implant body 120 is greater than the overall height (h2) of the posterior portion 123. In contrast, the overall height for the anterior and posterior portions for the central implant body 110 is similar. It is important to note that in other embodiments, the outer walls of the implant assembly 100, including each of the central implant body 110 and the superior and inferior implant bodies 120A and 120B, may not be lordotic. By way of example, the overall height (h1) for the anterior portion 121 for the superior or inferior implant body 120 may be equal to the overall height (h2) of the posterior portion 123.

Turning to FIGS. 5 and 6, identical fastening arrangements F1 and F2 (first and second) are provided along the inner margin regions of the upper and lower faces 1101 and 1102 of the central implant body. As a result, any of the superior and inferior implant bodies 120A and 120B may be fastened onto the upper face 1101 or the lower face 1102. Such an arrangement allows the superior and inferior implant bodies 120A and 120B to be interchangeably fastened onto either face of the central implant body 110. The central implant body 110 comprises a thicker anterior portion 111 and a relatively thinner posterior portion 113. Similarly, each of the superior and inferior implant bodies 120A and 120B (that have an identical and interchangeable configuration) also comprise respective thicker anterior portions 121 and relatively thinner posterior portions 123. The upper face 1101 of the central implant body 110 comprises a first pair of projection members 112A located on the thicker anterior portion 111 and a second pair of projection members 112B located on the relatively thinner posterior portion 113 of the central implant body. The projection members 112A and 112B are provided in the form of castellations about the inner margin (defining the passage 150) of the upper face 1101. Each of the superior and inferior implant bodies 120 comprises a vertebra engaging face 1201 (See FIG. 7A) and an implant engaging face 1202 (See FIG. 7B) for engaging the central implant body 110. The combination of the projection members 112A and 112B and the corresponding openings 122 comprises the fastening arrangements F1 and F2. The implant engaging face 1202 in each of the superior and inferior implant bodies 120 comprises respective pairs of projection receiving openings 122 that are structured to receive the pairs of projection members 112A and 112B on the upper face or lower face of the central implant body 110. The projection members 112A and 112B of the central implant body 110 and the corresponding openings 122 are arranged for allowing outer walls of the central implant body 110 and the superior and inferior implant bodies 120A and 120B to be interconnected, upon engagement, to provide a continuous outer surface (as shown in FIGS. 1 to 4).

In the preferred embodiment, the projections 112A and 112B of the central implant body 110 and the corresponding projection receiving openings 122 are arranged to ensure that each of the superior and inferior implant bodies 120A and 120B can be fastened to the central implant body 110 in no more than one fastened orientation to ensure that the central implant body 110 and the vertebra engaging implant bodies 120 fit together such that at least the inner walls of the internal passage 150 provide a continuous surface to define a continuous passage to promote growth of graft material. The fastened configuration also provides a continuous outer surface extending across the central implant body 110 and each of the superior and inferior implant bodies 120A and 120B, as shown in FIGS. 1 to 4.

It is important to note that in further embodiments, the projecting members 112A and 1120B may be provided on the superior or inferior implant bodies 120A and 120B and the projections receiving openings 122A and 122B may be provided on the upper and lower face of the central implant body 110 without departing from the spirit and scope of the invention.

Referring to FIG. 5 (including insets shown in FIGS. 5A and 5B) respective locking arrangements are provided for inter-locking the superior implant body 120A and the inferior implant body 120B with the upper and lower faces 1101 and 1102 of the central implant body 110. The locking arrangement comprises a pair of opposed projecting locking members 117A and 117B (generally denoted by reference numeral 117) located on the upper face 1101 and lower face 1102 of the central implant body 110. Each locking member 117A and 117B is located in between the opposed anterior and posterior portions 121 and 123. The locking members 117 are adapted to be received and retained into the respective locking recesses 127 provided on the implant engaging face 1202 for the superior or inferior implant body 120. Each locking recess 127 is defined by one or more recess walls.

Figure 5A:
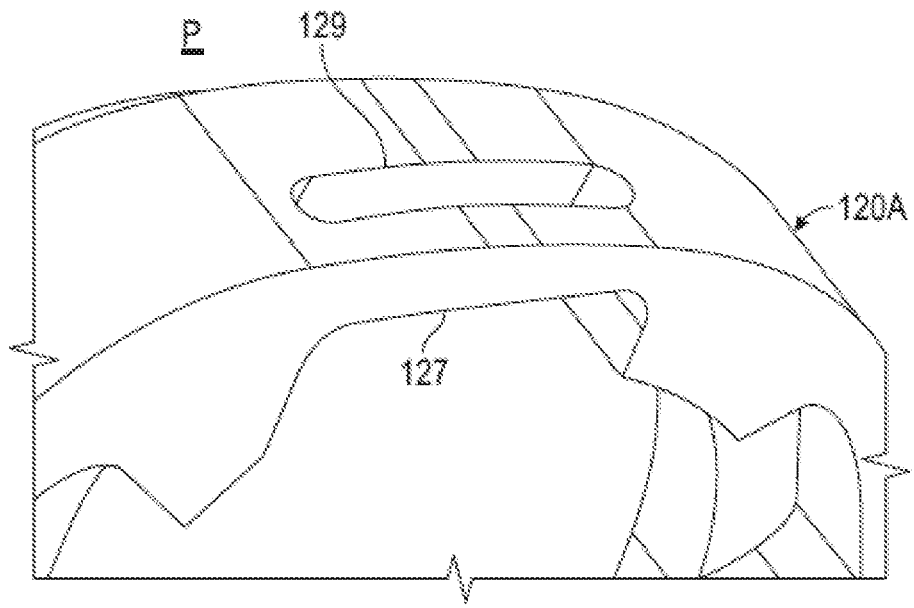
FIG. 5A is an enlarged view of inset P shown in FIG. 5.
Figure 5B:
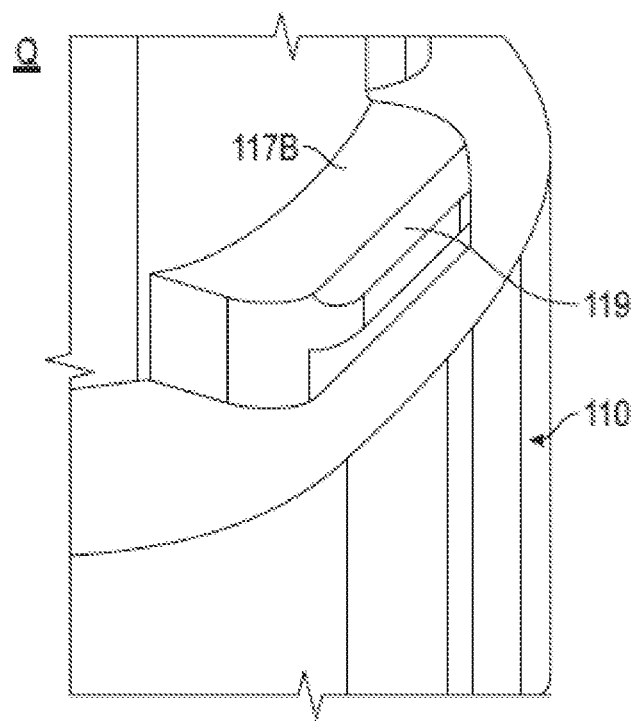
FIG. 5B is an enlarged view of inset Q shown in FIG. 5.

Turning to detailed views shown in FIGS. 5A and 5B, each locking member 117 comprises a profiled locking portion 119 adapted to be received and retained in a locking aperture such as slots 129 located in one of said recess walls defining the locking recess such that the locking member 117 can be press fitted into the locking recess 127 to push the profiled portion 119 into the slot 129 thereby inter-locking the central implant body 110 with the superior implant body 120A and/or the inferior implant body 120B. The provision of the locking arrangement comprising the locking members 117A and 117B in the preferred embodiment allows for reducing the possibility of inadvertent uncoupling of the central implant body 100 from the superior and inferior implant bodies 120A and 120B.

In other alternative embodiments, the locking members 117 may be provided along the implant engaging face 1202 of the superior or inferior implant body 120 and the locking recess may be provided on the upper face 1101 and the lower face 1102 of the central implant body 110 without departing from the spirit and scope of the invention.

The central implant body 110 may be provided with varying heights depending on the overall requirements. For example, the central implant body 110 may possess an overall height ranging from 8 mm to 100 mm or other heights. Similarly, the superior and inferior implant bodies 120 may be provided with an overall height ranging from 5 mm-50 mm or other heights. The provision of the fastening arrangement allows of a central implant body of a height (H1) to be combined in series with vertebra engaging implant bodies 120 of height (H2) to achieve an implant assembly 100 with an overall height of H3 (H3=H1+2H2). By way of example, in order to achieve an overall vertebral implant height of 20 mm, a central implant body 110 of height 10 mm may be combined with two of the vertebra engaging implant bodies 120, each having a height of 5 mm.

The three piece assembly of the presently described embodiment allows surgeons to select a central implant body 110 and two vertebra engaging implant bodies 120 and assemble these implant bodies in series to achieve a vertebral implant with a specific overall height.

It is important to appreciate that the presently described embodiment provides several advantages over the prior art. First, as explained in the earlier sections, positioning the fastening arrangement along an inner margin region of the upper and lower faces of the central implant body 110 allows for a greater volume of bone graft material to be introduced into passage 150. Secondly, the location of the fastening arrangement and the locking arrangement, as discussed in the earlier sections, provides much improved engagement between the implant bodies 110, 120A and 120B. Without wishing to be bound by theory, the inventors believe that locating the fastening arrangement along the inner margin (in a manner as previously described) improves the implant assembly's overall tolerance to sideways relative movement between each of the implant bodies 110, 120A and 120B.

The following passages describe a non-limiting surgical method for implanting the vertebral column implant assembly 100. Once the surgeon has surgically removed, the vertebral body/s and intervertebral discs the surgeon will template the corpectomy defect with a templating instrument. The templating instrument provides an indication of the overall height required for the vertical column implant assembly 100 that is required to fill the corpectomy defect. Once the overall height has been determined by the templating instrument reference is then made to a sizing chart to select the appropriate implant bodies ie the central implant body 110, the superior implant body 120A and the inferior implant body 120B.

As has been previously discussed in the earlier sections, the aforementioned structural configuration of the vertebral column implant assembly 100 allows surgeons to select a central implant body 110 (of a specific height) and two vertebra engaging implant bodies 120A and 20B (also having specific heights) and assemble these implant bodies in series to achieve a vertebral implant with a specific overall height that is identical to the desired height for filling the corpectomy defect. The implant components 110, 120A and 120B are fastened to each other using the fastening arrangements F1 and F2 and the assembled implant 100 is inserted by the surgeon to fill the corpectomy defect.

In compliance with the statute, the invention has been described in language more or less specific to structural or methodical features. The term "comprises" and its variations, such as "comprising" and "comprised of" is used throughout in an inclusive sense and not to the exclusion of any additional features.

It is to be understood that the invention is not limited to specific features shown or described since the means herein described comprises preferred forms of putting the invention into effect.

The invention is, therefore, claimed in any of its forms or modifications within the proper scope of the appended claims appropriately interpreted by those skilled in the art.

The invention claimed is:

1. A vertebral column implant assembly for insertion between two vertebrae, the assembly comprising:
   a superior implant body for engagement with a superior vertebra;
   an inferior implant body for engagement with an inferior vertebra;
   a central implant body adapted to be positioned in between the superior implant body and the inferior implant body, the central implant body further comprising:
      a first fastener positioned on an upper face of the central implant body to engage and fasten the superior implant body, wherein the first fastener comprises a first plurality of projection formations; and
      a second fastener positioned on a lower face of the central implant body to engage and fasten the inferior implant body, wherein the second fastener comprises a second plurality of projection formations;
   wherein each of the central implant body, the superior implant body and the inferior implant body comprises internal walls defining respective passages, such that the first and second fasteners engage inner marginal portions of the superior and inferior implant bodies respectively and are positioned on the central implant body to engage and fasten the superior and inferior implant bodies respectively to interconnect each of the respective internal walls and passages to form a continuous internal wall defining a single, linear continuous passage to allow graft material to be positioned therein; and
   wherein each of the first plurality of projection formations and the second plurality of projection formations forms castellations about an inner margin of the upper face and lower face respectively and wherein the first plurality of projection formations is receivable into projection formation receiving portions positioned along an in-use lower portion of the superior implant body and the second plurality of projection formations is receivable into projection formation receiving portions positioned along an in-use upper portion of the inferior implant body to define a portion of the continuous internal wall defining the single, linear continuous passage, and wherein the first plurality of projection formations includes at least one projection lock being located along a radially outward location of the upper face and configured to lock to a complementary lock on the superior implant body and wherein the second plurality of projection formations includes at least one projection lock being located along a radially outward location of the lower face and configured to lock to a complementary lock on the inferior implant body.

2. A vertebral column implant assembly in accordance with claim 1 wherein the first fastener of the central implant body further comprises: a first plurality of receiving portions adapted to receive projection formations positioned along the in-use lower portion of the superior implant body; and wherein the second fastener comprises a second plurality of receiving portions adapted to receive projection formations positioned along the in-use upper portion of the inferior implant body.

3. A vertebral column implant assembly in accordance with claim 1 wherein each of said first and second fastener is adapted for securing the central implant body to said superior and inferior implant bodies respectively to prevent relative movement between the central implant body and said superior and inferior implant bodies.

4. A vertebral column implant assembly in accordance with claim 1 wherein each of said central implant body and said superior and inferior implant bodies comprises respective outer walls such that upon fastening the central implant body to the superior and inferior implant bodies, the respective outer walls become inter-connected to provide a continuous outer surface.

5. A vertebral column implant assembly in accordance with claim 1 wherein the first fastener allows the superior implant body to be fastened to the central implant body in no more than one fastened orientation.

6. A vertebral column implant assembly in accordance with claim 1 wherein the second fastener allows the inferior implant body to be fastened to the central implant body in no more than one fastened orientation.

7. A vertebral column implant assembly in accordance with claim 1 wherein the superior and inferior implant bodies are interchangeable such that the first fastener is adapted to engage the inferior implant body; and wherein the second fastener is adapted to engage the superior implant body.

8. A vertebral column implant assembly in accordance with claim 1 wherein each of said central implant body and the superior and inferior implant bodies comprises a respective anterior portion having an anterior wall and a posterior portion having a posterior wall with opposed intermediate portions extending between said anterior and posterior portions.

9. A vertebral column implant assembly in accordance with claim 8 wherein a length for each of the anterior walls is equal to or greater than a length for the posterior walls.

10. A vertebral column implant assembly in accordance with claim 8 wherein a height for the anterior portion for the superior implant body is equal to or greater than a height for the posterior portion of the superior implant body.

11. A vertebral column implant assembly in accordance with claim 8 wherein a height for the anterior portion of the inferior implant body is equal to or greater than a height for the posterior portion of the inferior implant body.

12. A vertebral column implant assembly in accordance with claim 8 wherein each of the respective posterior portions of the central implant body and the superior and inferior implant bodies comprises the posterior wall having a thickness t1 and wherein each of the respective anterior portions of the central implant body and the superior and inferior implant bodies comprises the anterior wall having a thickness t2 greater than t1.

13. A vertebral column implant assembly in accordance with claim 1 wherein the one or more projection locks that are located along a radially outward location of the upper face and the one or more projection locks that are located along the radially outward location of the lower face are adapted to be received into corresponding locking recesses defined by one or more recess walls.

14. A vertebral column implant assembly in accordance with claim 13 wherein the one or more projection locks comprise a profiled locking portion adapted to be received and retained in a locking aperture located in one of said recess walls defining the locking recess such that the projection locks can be press fitted into the locking recess thereby inter-locking the central implant body with the superior implant body and/or the inferior implant body.

15. A vertebral column implant assembly in accordance with claim 13 wherein each of the locking recesses are positioned in the in-use lower portion of the superior implant body and/or the in-use upper portion of the inferior implant body.

16. A vertebral column implant assembly in accordance with claim 13 wherein each of said central implant body and the superior and inferior implant bodies comprises a respective anterior portion having an anterior wall and a posterior portion having a posterior wall with opposed intermediate portions extending between said anterior and posterior portions and wherein each of said projection locks is located in between said anterior and posterior portions of the central implant body and wherein the locking recesses are located in between the anterior and posterior portions of the superior implant body or the inferior implant body.

* * * * *